(12) United States Patent
Drobnik et al.

(10) Patent No.: US 7,588,528 B2
(45) Date of Patent: *Sep. 15, 2009

(54) BRACHYTHERAPY APPARATUS FOR DISPENSING MEDICATION

(75) Inventors: Christopher D. Drobnik, Wauconda, IL (US); Michael W. Drobnik, Downers Grove, IL (US)

(73) Assignee: C. R. Bard, Inc., Murray Hill, NJ (US)

( * ) Notice: Subject to any disclaimer, the term of this patent is extended or adjusted under 35 U.S.C. 154(b) by 392 days.

This patent is subject to a terminal disclaimer.

(21) Appl. No.: 10/924,441

(22) Filed: Aug. 24, 2004

(65) Prior Publication Data

US 2006/0063961 A1    Mar. 23, 2006

(51) Int. Cl.
*A61N 5/00*    (2006.01)
(52) U.S. Cl. ............................................. 600/3; 600/7
(58) Field of Classification Search .................. 600/1–8
See application file for complete search history.

(56) References Cited

U.S. PATENT DOCUMENTS

| | | | |
|---|---|---|---|
| 2,153,889 A | 4/1939 | Hames et al. | |
| 3,351,049 A | 11/1967 | Lawrence | |
| 3,670,729 A | * 6/1972 | Bennett et al. | 604/500 |
| 4,402,308 A | 9/1983 | Scott | |
| 4,447,223 A | 5/1984 | Kaye et al. | |
| 4,451,254 A | 5/1984 | Dinius et al. | |
| 4,697,575 A | 10/1987 | Horowitz | |
| 4,754,745 A | 7/1988 | Horowitz | |
| 4,815,449 A | 3/1989 | Horowitz | |
| 5,147,295 A | 9/1992 | Stewart | |
| 5,242,373 A | 9/1993 | Scott | |
| 5,460,592 A | 10/1995 | Langton et al. | |
| 5,928,130 A | 7/1999 | Schmidt | |
| 6,007,474 A | 12/1999 | Rydell | |
| 6,010,446 A | 1/2000 | Grimm | |
| 6,095,967 A | 8/2000 | Black et al. | |
| 6,264,600 B1 | 7/2001 | Grimm | |
| 6,270,472 B1 | 8/2001 | Antaki et al. | |
| 6,358,195 B1 | 3/2002 | Green et al. | |

(Continued)

OTHER PUBLICATIONS

Novel and Inexpensive System for Interstitial I125 Seed Implants, William L. DeGinder and Vitthalbhai D. Mistry, Int. J. Radiation Oncology Biol. Phys., vol. 4, pp. 745-747, Pergamon Press Inc. 1978.

(Continued)

*Primary Examiner*—John P Lacyk
(74) *Attorney, Agent, or Firm*—Carmen Patti Law Group, LLC (57) ABSTRACT

An applicator system for interstitial radiation therapy that uses a brachytherapy needle assembly for simultaneously dispensing an effective amount of medicine, such as anti-inflammatory agents, along with radioactive seeds. A medicine cartridge or a modified seed cartridge, having a reservoir on its proximal end, can be attached to the applicator body for dispensing medicine into a needle or medicine can be injected into the needle via a three-way fitting attached to the applicator body. Alternatively, a modified stylet having a reservoir on its proximal end containing medicine can be used to deliver medication to a needle. Additionally, the brachytherapy needle or the radioactive seeds and spacers can be coated with medication that would be absorbed by the body upon implantation.

22 Claims, 4 Drawing Sheets

U.S. PATENT DOCUMENTS

| | | |
|---|---|---|
| 6,450,937 B1 | 9/2002 | Mercerau et al. |
| 6,514,193 B2 | 2/2003 | Kaplan |
| 6,554,760 B2 | 4/2003 | Lamoureaux et al. |
| 6,561,967 B2 | 5/2003 | Schmidt |
| 6,572,525 B1 | 6/2003 | Yoshizumi |
| 6,575,890 B2 | 6/2003 | Kaplan et al. |
| 6,616,593 B1 | 9/2003 | Elliott et al. |
| 6,626,817 B2 | 9/2003 | Luth |
| 6,638,206 B2 | 10/2003 | Green et al. |
| 6,656,107 B1 | 12/2003 | Pederson et al. |
| 6,669,622 B2 | 12/2003 | Reed et al. |
| 6,723,037 B2 | 4/2004 | Hamazaki et al. |
| 6,746,661 B2 | 6/2004 | Kaplan |
| 6,761,680 B2 | 7/2004 | Terwilliger et al. |
| 2002/0169354 A1 | 11/2002 | Munro, III |
| 2002/0180096 A1 | 12/2002 | Karl et al. |
| 2003/0064965 A1* | 4/2003 | Richter ................... 514/102 |
| 2003/0084988 A1 | 5/2003 | Terwilliger et al. |
| 2003/0088140 A1 | 5/2003 | Terwilliger et al. |
| 2003/0088141 A1 | 5/2003 | Terwilliger et al. |
| 2003/0088144 A1 | 5/2003 | Terwilliger et al. |
| 2003/0092958 A1 | 5/2003 | Terwilliger et al. |
| 2003/0097035 A1 | 5/2003 | Tucker et al. |
| 2003/0171637 A1 | 9/2003 | Terwilliger et al. |
| 2004/0019381 A1 | 1/2004 | Pflueger |

OTHER PUBLICATIONS

International Search Report No. PCT/US2005/28134 dated Dec. 9, 2005.

Written Opinion of the International Searching Authority dated Dec. 9, 2005.

* cited by examiner

BRACHYTHERAPY APPARATUS FOR DISPENSING MEDICATION

BACKGROUND OF INVENTION

The invention relates generally to brachytherapy needles and more particularly to applicators that dispense both medication and radioactive seeds.

Brachytherapy refers to a localized method of treating cancer that places radioactive sources directly within tissue. The advantage of brachytherapy is that very high doses of ionizing radiation are delivered to a localized area such that the radiation is supplied primarily to the treatment area without significantly affecting tissues throughout the body. This ability, when combined with a rapid reduction in the radiation dose as a function of distance, shields distant anatomies from unwanted radiation. Hence, the technique has provided excellent results for localized treatment of various tumors.

Brachytherapy seeds for treating prostate cancer are implanted from needles, which are inserted through the perineum into the prostate gland. Appropriate needle placement can be determined based on the special three-dimensional distribution specified in a dosimetry plan and is commonly executed using a guiding template or grid to guide needle placement. Placement techniques of brachytherapy seeds vary, but generally, the seeds are placed using preloaded needles, containing both radioactive seeds and optionally spacers, which position the seeds along a row in accordance with the dosimetry plan. A movable stylus can be positioned within the needle against the assembly of seeds and spacers. Once the needle is properly positioned in the prostate, the needle can then be removed over the stylus, leaving the seeds (and spacers) in place. Alternatively, seeds can be placed using a mechanical applicator system, such as that available from Mick Radio-Nuclear Instrument, Inc. ("MRNI") of Mount Vernon, N.Y. The applicator system, disclosed in U.S. Pat. No. 5,860,909 to Mick, et al. and incorporated herein by reference, allows for individual seed placement without the use of inactive spacers.

In the applicator system, one or more seed cartridges or "magazines" may supply seeds to a needle or multiple needles as necessary. These cartridges may contain up to fifteen seeds or more and are attached to the applicator. The applicator can be fixed to a needle and designed to implant a single seed by ejecting it from the distal end of the needle, which has been placed in the prostate gland in accordance with the dosimetry plan. As a seed is placed, a physician can position the needle for the placement of other seeds.

The use of multiple needles breaking through the skin and tissue and leaving behind foreign objects can lead to adverse reactions and trauma to the surrounding area. Control of trauma, bleeding and swelling during and after a brachytherapy implant procedure has long been a goal of practitioners. For example, swelling of the prostate and surrounding tissue can displace the seeds and lead to uncontrolled doses of radiation, which can involve some zones that are unintentionally hot and some that are undesirably, and possibly dangerously, cold.

Trauma and swelling are commonly treated by administering systemic drugs to the patient. This has the disadvantage of requiring enough drug to be dispersed throughout the body, even though the trauma and swelling are localized. This can delay the effectiveness of the drugs.

Additional known prior art devices used to deliver seeds are disclosed in U.S. Pat. Nos. 4,402,308 to Scott, 4,697,575 to Horowitz, and 5,938,583 to Grimm, which are incorporated herein by reference. Conventional devices used for storing and delivering radioactive seeds are also described in U.S. Pat. No. 4,086,914 to Moore and U.S. Pat. No. 4,167,179 to Kirsch, which are incorporated herein by reference. However, none of these references adequately disclose methods of treating and addressing the trauma and swelling that can occur at the implantation site.

Accordingly, a need exists for improved treatment of trauma and swelling to tissue caused by a brachytherapy needle implant procedure.

SUMMARY OF THE INVENTION

Generally speaking, in accordance with the invention, a brachytherapy needle is provided to dispense an effective amount of medication, preferably an anti-inflammatory drug, at the approximate time brachytherapy radiation sources are implanted, such a needle can be fit with a seed cartridge, wherein seeds are dispensed one at a time. A stylet is used to push a seed from the needle tip, then retracted, so that a new seed is dispensed to the needle for implantation. The invention herein described would allow for the dispensing of an effective amount of medication, such as anti-inflammatory agents, chemotherapy agents, clotting agents, anesthetics, steroids and the like, along with radioactive seeds, and optionally, spacers. A needle could contain one or more drugs, chosen by the physician and would dispense the medicine approximately simultaneously with at least one radiation source as they are ejected from the needle. Procedures in accordance with the invention would allow for the administration of medicine selected by a physician at the time of an implant procedure. Thus, both radiation sources and medication can be dispensed with only one needle insertion.

In one embodiment of the invention, an effective amount of medication is delivered via a three-way fitting on the body of an applicator having an implantation needle, such as a Mick applicator, where a cartridge delivers seeds to a needle. In a second embodiment of the invention, a medicine cartridge is attached to the body of such an applicator and dispenses liquid or solid medication to the implantation site via the implantation needle. In a third embodiment of the invention, a modified seed cartridge that dispenses both seeds and medication to the implantation needle is attached to the body of the applicator. In a fourth embodiment of the invention, the implantation needle is coated with medication that would be absorbed by the body during implantation or the implantation needle is flushed with medication to coat radiation sources prior to implantation in the body. In a fifth embodiment of the invention, the seeds themselves are coated with medication that would be absorbed by the body during implantation. In a sixth embodiment of the invention, the needle cannula is constructed with a dual lumen such that the one lumen dispenses the radioactive seeds and the second lumen dispenses the medication. In a seventh embodiment of the invention, the medication is in a medicine container, similar to the size of the seeds, and is loaded and dispensed with the radioactive seeds upon implantation. In an eighth embodiment of the invention, the seed applicator is attached to an external device by a tether, the tether being fitted to carry medication from the external device to the body of the applicator for dispensing along with the seeds. In a another embodiment of the invention, the seed cartridge is dipped into medication immediately prior to implantation, thereby coating the seeds with an effective amount of medication.

Accordingly, it is an object of this invention to provide an improved system and method for the administration of medicine to treat trauma caused by brachytherapy techniques.

Still other objects and advantages of the invention will in part be obvious and will in part be apparent from the specification.

The invention accordingly comprises the several steps and the relation of one or more of such steps with respect to each of the others, and the apparatus possessing the features, properties, and the relation of elements, which are exemplified in the following detailed disclosure, and the scope of the invention will be indicated in the claims.

BRIEF DESCRIPTION OF THE DRAWINGS

For a fuller understanding of the invention, reference is had to the following description, taken in connection with the accompanying drawings, in which.

The drawings are not necessarily to scale. The relative sizing depicted was chosen to more clearly depict various aspects and details of the invention. Also, similar structures are assigned the same reference numerals.

DETAILED DESCRIPTION OF THE PREFERRED EMBODIMENTS

Figure 1:
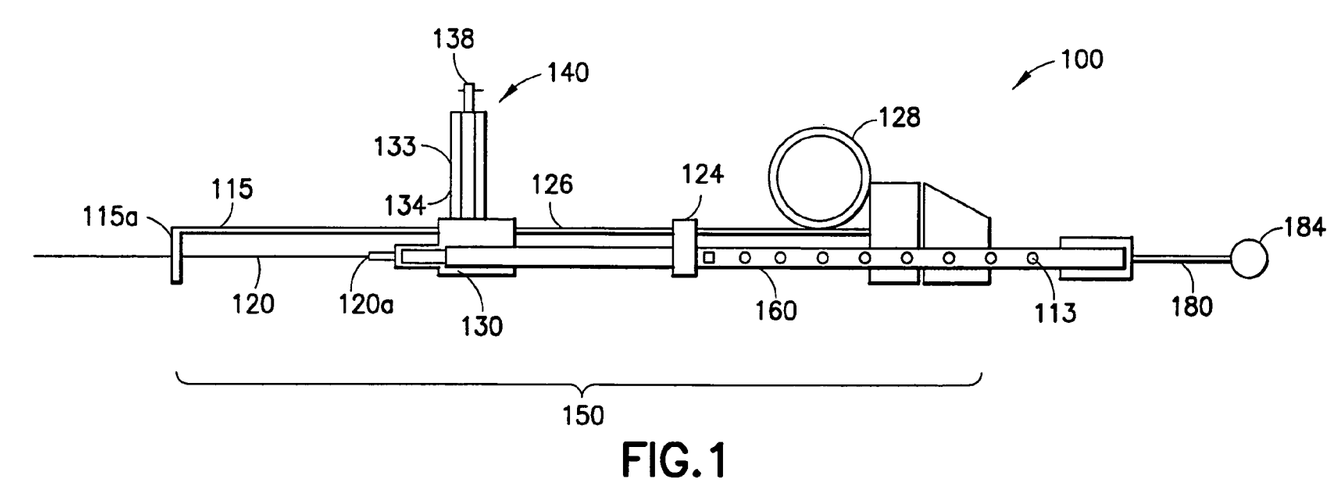
FIG. 1 is a side view of an applicator in accordance with an embodiment of the invention.

An applicator of medication, preferably anti-inflammatory medication and brachytherapy sources 100, in accordance with an embodiment of the invention is shown generally in FIG. 1. Applicator 100 includes a hollow needle 120 insertable into the patient's body, a needle chuck 130 for releasably receiving and holding needle 120, a magazine 140 for holding and dispensing brachytherapy seeds into needle chuck 130, a main barrel 160 connected to chuck 130, and a stylet pushrod 180, extendable through main barrel 160, chuck 130, and the bore of needle 120. Applicator 100 also includes a base frame member 115 along which needle 120, needle chuck 130, magazine 140 and main barrel 160 are slidably mounted. Frame member 115 includes an abutment end 115a adapted to abut a surface of a patient's body or a template grid (not shown) fixed with respect to the patient's body, a barrel collar 124 through which main barrel 160 is slidable, and two rods 126 extending between and attached to abutment end 115a and collar 124. One or more finger rings 128 for receiving a user's fingers are mounted on collar 124.

Applicator 100 is designed to allow needle 120 to be moved incrementally with respect to abutment end 115a of base frame 115 and therefore, to be moved incrementally with respect to the patient's body. For this purpose, main barrel 160 includes a plurality of annular notches or indentations 130 that are equally spaced along the length of barrel 160. A spring-loaded ball plunger (not shown) or the like, mounted in barrel collar 124 can be successively seated in each indentation 113 as main barrel 160 is moved through collar 124. As the plunger engages each indentation 113, barrel 160 is releasably fixed in collar 124, and the user is provided with a tactile and/or audible indication of the distance moved by barrel 160. This procedure can also be performed in other ways, such as by observing graduation lines on the outside of the needle. Accordingly, the tip of needle 120, which moves with barrel 160, can be retracted from the patient's body in a series of discrete distances equal to the distances separating indentations 113 on barrel 160.

Applicator 100 also includes a magazine 140, which includes a magazine head 133 and a seed cartridge 134 in which seeds are stacked parallel to each other. A spring-loaded magazine plunger 138 is biased against the seeds at the upper end of magazine 110 to facilitate seed movement into needle chuck 130 and to provide an indication to the operator that a seed has been dispensed from cartridge 134.

Stylet 180, which is extendable through the bores of main barrel 160, needle chuck 130, and needle 120, includes a stylet handle 184 at its proximal end. Handle 184 can be held by an operator to control movement of stylet 180 during use.

To use applicator 100, a plurality of needles 120 are inserted into the patient's prostate gland in areas where rows of seeds are to be implanted. The outside surface or bore of needle 120 can be coated or flushed with medication prior to use, thereby permitting direct application of medication while dispensing seeds to the implantation site. A template (not shown) may be used to facilitate positioning of needles 120. Then, needle chuck 130 is coupled with the protruding end 120a of one needle 120. Stylet 180, which can be initially fully extended in needle 120 to for example, dispense medication in liquid, tablet or capsule form, is retracted from needle 120 and needle chuck 130. Based on the action of magazine 140, this can cause a seed from magazine 140 to be transferred in chuck 130 for movement into needle 120. Stylet 180 is then pushed through barrel 160 and chuck 130 against the seed, advancing the seed through needle 120 and into the prostate gland at a precise position at the tip of needle 120. When stylet 180 is retracted, another seed is moved into chuck 130. At the same time, extended magazine plunger 138 will move further into magazine 140, which movement will indicate to the operator that a seed has been positioned in chuck 130 for transfer into needle 120.

After a first seed has been implanted, needle 120 can be partly retracted from the patient's body a selected number of notches so that the next seed implanted is spaced a selected distance apart from the first seed. Needle 120 is withdrawn by retracting main barrel 160 through the barrel collar 124 until ball plunger in the collar 124 engages the next indentation 113 in the barrel 160. As previously noted, this provides the operator with a tactile and/or audible indication that the needle is in position for another seed implant. Then, stylet 180 is again retracted to enable the next seed from magazine 140 to be positioned for movement into needle 120. Stylet 180 is then advanced through needle 120 to force the next seed into the patient's body at a distance away from the first seed corresponding to the distance between the barrel indentations 113. This procedure is repeated for subsequent seed implants. It should also be made clear that other devices for implanting seeds can be modified in accordance with the invention to deliver medication, such as anti-inflammatory medication to the seed implantation site.

Figure 2:
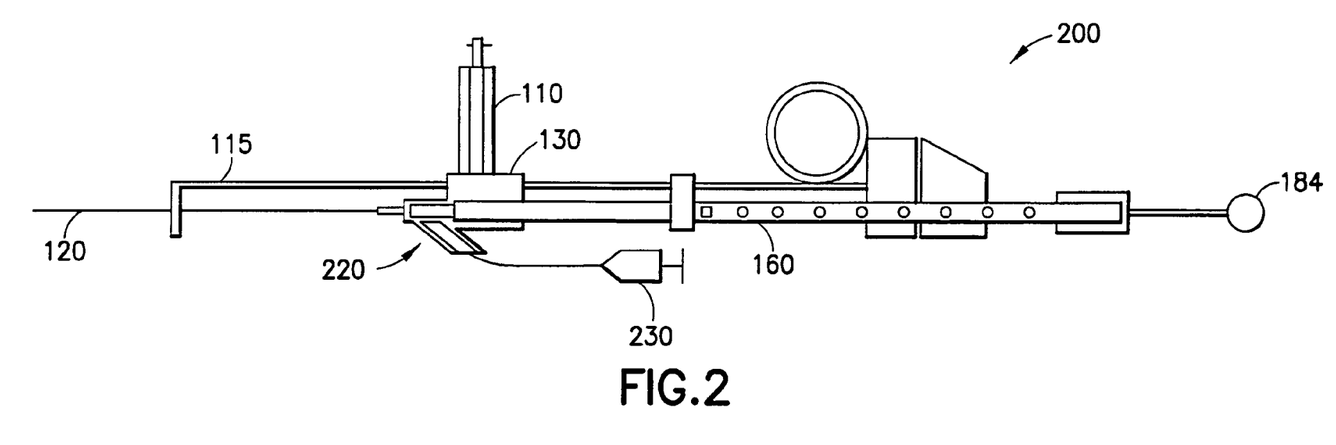
FIG. 2 is a side view of a three way fitting attached to the body of an applicator in accordance with an embodiment of the invention.

A device for simultaneously delivering brachytherapy seeds and anti-trauma or other medicine in accordance with another preferred embodiment of the invention is shown generally as applicator system 200 in FIG. 2, with like reference numerals assigned to similar structures. A three-way fitting 220 is attached to needle chuck 130 of applicator system 200. An effective selected amount of medication is delivered to the desired location by inserting a syringe 230 or similar device loaded with medication, into fitting 220 and ejecting the medication either before, during or after radioactive sources (not shown) are ejected. An effective amount of medication can also be added directly to the cannula of needle 120 holding radioactive sources, such seeds, to be dispensed simultaneously with same.

Figure 3:
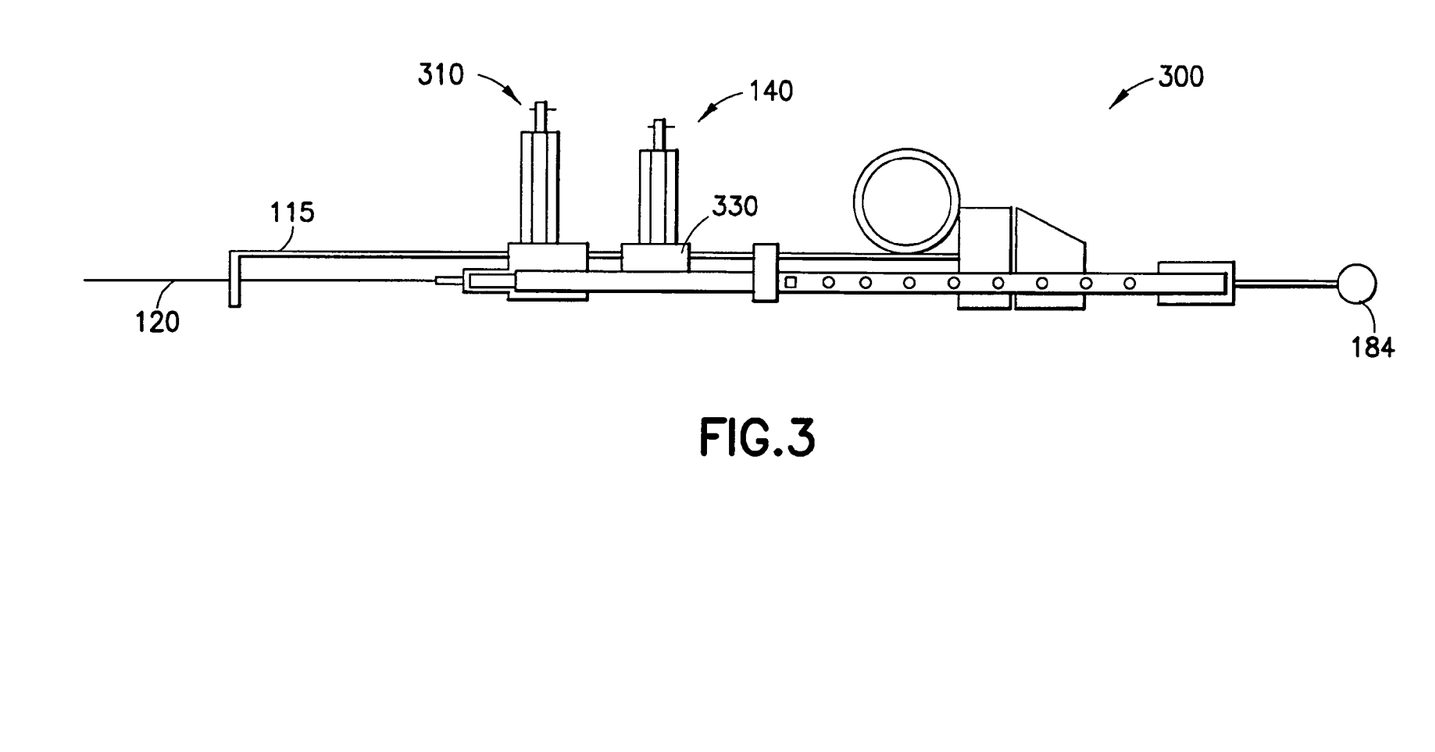
FIG. 3 is a side view of a medicine cartridge attached to the body of an applicator in accordance with an embodiment of the invention.

Another system for the direct delivery of medicine and brachytherapy seeds to the same location in accordance with an embodiment of the invention is shown generally as applicator system 300 in FIG. 3. Medication can be stored in a medicine cartridge/reservoir 310 fitted to be attached to needle chuck 330 of the applicator system alongside seed cartridge 120. Chuck 330 is similar to chuck 130 and cartridge/magazine 310 is similar to cartridge/magazine 140. One difference is that cartridge 330 is loaded with medication. This can be in the form of seed sized containers or medication soaked spacer elements. These would be ejected in the same manner as seeds, discussed above. In another embodiment of the invention, cartridge 310 would include a brush-like structure to coat seeds as they are passed towards needle 120 by stylet 180.

Figure 4:
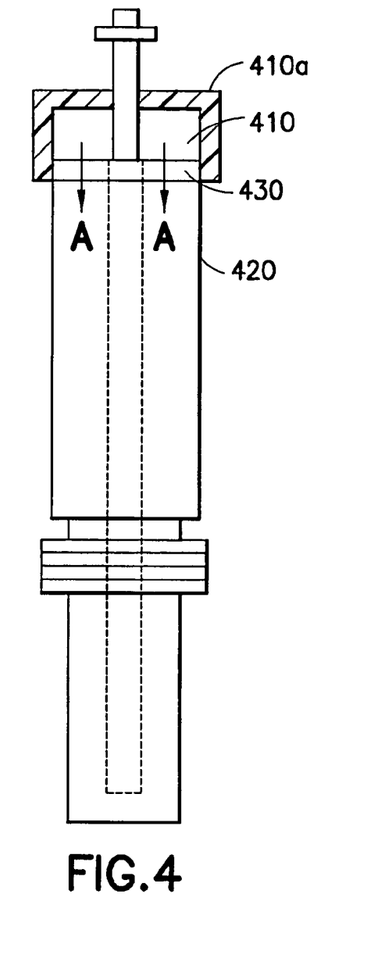
FIG. 4 is a cross-sectional view of a modified seed cartridge in accordance with an embodiment of the invention.

Another apparatus for use in the direct delivery of medicine and brachytherapy seeds to the same location in accordance with an embodiment of the invention is shown generally as modified seed cartridge 400 in FIG. 4. Seed cartridge 400 is modified above a seed holder 420 to add a reservoir 410 for containing and dispensing medication. Reservoir 410 acts as a temporary storage structure. As the seeds (not shown) are dispensed, medication can be simultaneously dispensed from reservoir 410. Reservoir 410 can be in the form of an elastic bulb, such as one used for a large dropper with an elastic wall 410a, or other similar-type structure and can have a volume of up to 1 ml, or larger. Reservoir 410 can be depressed, being that it is a collapsible and resilient container. A fluid passage exists to seed holder 420 allowing for the contents of reservoir 410 to flow in the direction of arrows A. A seal 430 can be provided to prevent the outflow of liquids. An end user or a manufacturer can draw an effective amount of medication into reservoir 410 for delivery.

Figure 5:
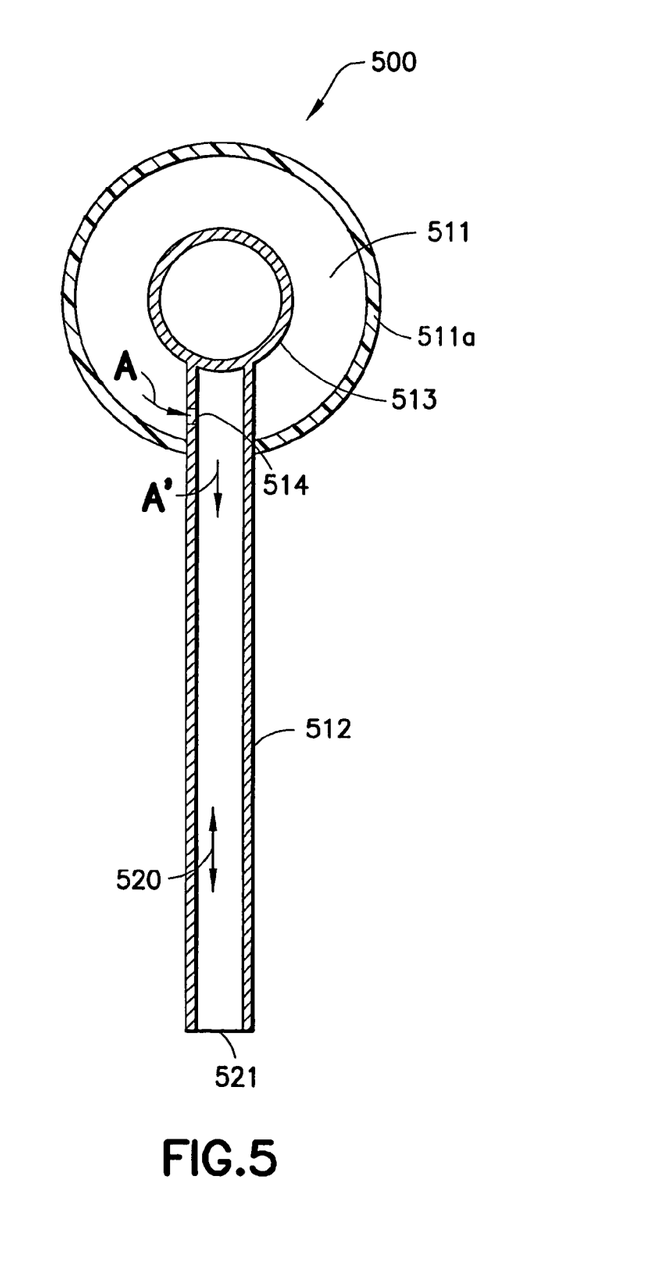
FIG. 5 is a cross-sectional view of a modified stylet in accordance with an embodiment of the invention.

Another system for the direct delivery of medicine and brachytherapy seeds to the same location in accordance with an embodiment of the invention is shown generally as modified stylet 500 in FIG. 5. Modified stylet 500 is formed with a hollow shaft 512 and a handle 513. Stylet 500 is sized to fit within a needle lumen so that sources can be dispensed by moving stylet 500 relative to a needle. A medicine reservoir 511 is joined to a stylet handle 513. Reservoir 511 acts as a temporary storage structure and can have a volume of up to 1 ml, or larger. Reservoir 511 is in the form of an elastic dropper bulb and can be depressed, being that it is a collapsible and resilient container. Reservoir 511 has a fluid passage 514 to a stylet lumen 520. Stylet lumen 520 and passage 514 allows medication to pass in the direction of arrows A and A' from stylet reservoir 511, through lumen 520 to be dispensed through lumen end 521 concurrently, before or after seeds and spacers (not shown) located in the needle cannula. An end user or a manufacturer can draw an effective amount of medication into attached reservoir 511 for delivery. Reservoir 511 can be a bulb, syringe or any other similar-type structure. An effective amount of medication can also be added directly to cannula holding seeds and spacers to be dispensed simultaneously with same.

Figure 6:
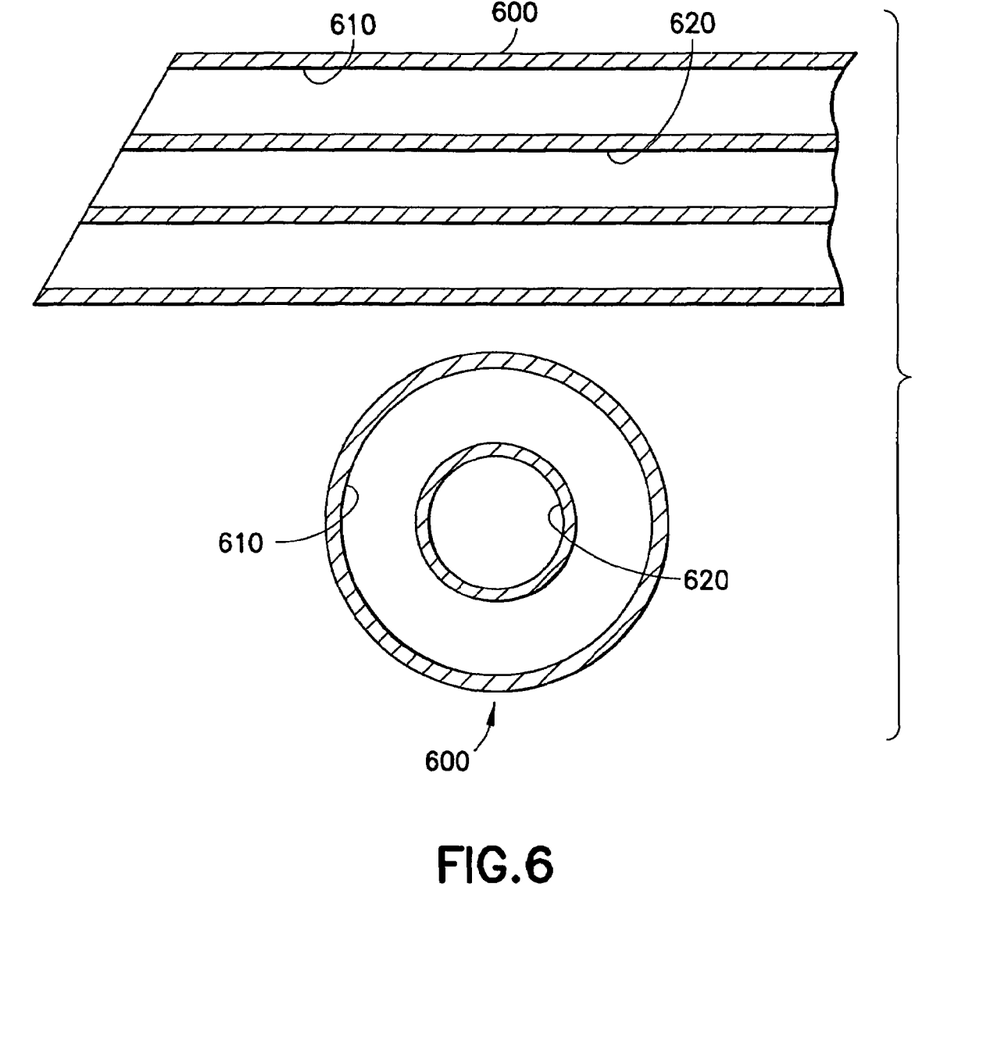
FIG. 6 is a frontal view of a dual lumen cannula in accordance with an embodiment of the invention.

Another system for the direct delivery of medicine and brachytherapy seeds to the same location in accordance with an embodiment of the invention is shown generally as dual lumen cannula in FIG. 6. Needle cannula 600 can be constructed with a dual lumen such that an inner lumen 620 contains at least one radioactive source and an outer lumen 610 is in fluid communication with a reservoir storing medication. Upon implantation, the contents of inner lumen 620 and outer lumen 610 are dispensed simultaneously or sequentially. The medication can be ejected from outer lumen 610 by squeezing a coupled bulb or by advancing a plunger.

An effective amount of medication can also be provided in a container. The material of construction of the packet should be bioabsorbable. Any bioabsorbable polymer can be used. The medicine container fits inside the lumen of a needle 120. The containers are then loaded and dispensed with the radioactive seeds upon implantation. In another embodiment, the applicator can be attached to an external device by a tether, the tether being fitted to carry medication from the external device to the body of the applicator for dispensing along with the seeds in response to a trigger. Alternatively, seeds in cartridge 110 can be dipped into medication immediately prior to implantation, thereby coating the radioactive seeds with medication.

Suitable anti-inflammatory agents that can be used include but are not limited to Ibuprofen (Motrin®, Advil®), Naproxen (Naprosyn®, Alleve®), Valdecoxib (Bextra®), Floctafenine (Idarac®), Ketoprofen (Orudis®, Oruvail®), Mefenamic Acid (Ponstel®), Nabumetone (Relafen®), Indomethacin (Indocin®), Diclofenac (Cataflam® and Voltaren®), Diflunisal (Dolobid®), Sulindac (Clinoril®), Flurbiprofen (Ansaid®), Oxaprozin (Daypro®), Fenoprofen (Nalfon®), Meclofenamate (Meclomen®), Etodolac (Lodine®), Piroxicam (Feldene®), Phenylbutazone (Cotylbutazone®), Tolmetin (Tolectin®), Meloxicam (Mobic®), Ketorolac (Toradol®), Nabumetone (Relafen®), Sulindac (Clinoril), Celecoxib (Celebrex®) and Rofecoxib (Vioxx®). Suitable doses can be calculated depending on the properties of each of the anti-inflammatory agents to provide an effective anti-inflammatory effect to the implantation site.

Suitable chemotherapy drugs that can be used include but are not limited to alkylating drugs such as cyclophosphamide, antimetabolites such as 5-fluorouracil (5-FU), antitumor antibiotics such as doxorubicin and bleomycin, plant alkaloids such as vinblastine and vincristine and steroid hormones such as tamoxifen. Effective doses are those that provide anti-cancer activity.

Suitable seeds can be of various types having low energy and low half-life such as Iodine seeds, known as I-125 seeds, consisting of a welded titanium capsule containing iodine 125 absorbed on a silver rod, or Palladium 103 seeds. Additionally, seeds can be manufactured using iridium 192, cesium 131, gold 198, yttrium 90 and phosphorus 32. Other types of seeds can be used such as those described in U.S. Pat. No. 6,248,057 to Mavity et al., which patent is incorporated herein by reference effective dosages are typically calculated as part of a prescribed treatment plan. Suitable spacers, if used can be made of bioabsorbable polymers.

A method for using a brachytherapy applicator system for simultaneously dispensing an effective amount of medication along with radioactive seeds and spacers comprises the use of a brachytherapy applicator system in any manner herein described, inserting the brachytherapy needle into a predetermined location, and implanting the radioactive seeds, optional spacers and an effective amount of medication directly to the implantation site.

It will thus be seen that the objects set forth above, among those made apparent from the preceding description, are efficiently attained and since certain changes may be made in the above construction without departing from the spirit and scope of the invention, it is intended that all matter contained in the above description or shown in the accompanying drawings shall be interpreted as illustrative and not in a limiting sense.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

It is also to be understood that the following claims are intended to cover all of the generic specific features of the invention herein described and all statements of the scope of the invention which, as a matter of language, might be said to fall there between.

What is claimed is:

1. A method of performing a brachytherapy procedure with an applicator system comprising a needle and a seed cartridge attached to the needle, the method comprising:
   inserting a brachytherapy needle having a lumen into a desired location in a patient along an insertion path extending from a proximal initial insertion point to a distal needle endpoint;
   dispensing at least one radiation source from the seed cartridge into the lumen of the brachytherapy needle, then from the brachytherapy needle to a location in the insertion path; and
   dispensing medication, separate from said at least one radiation source, from the lumen of the brachytherapy needle to a location in the insertion path before the brachytherapy needle is removed from the insertion path.

2. The method of claim 1, wherein the medication comprises an anti-inflammatory material.

3. The method of claim 1, wherein the medication comprises an anesthetic.

4. The method of claim 1, further comprising dispensing medication from a second cartridge to the needle for dispensing to the insertion path.

5. The method of claim 1, further comprising dispensing liquid medication from a reservoir coupled to a three-way fitting attached to a chuck of the needle.

6. The method of claim 1, further comprising coating the needle with medication.

7. The method of claim 1, further comprising dispensing medication from said seed cartridge, said seed cartridge having a medicine reservoir for holding and dispensing said medication and at least one radiation source into a chuck of the needle.

8. The method of claim 1, wherein the applicator system comprises a hollow stylet having a reservoir in fluid communication with the proximal end of the stylet, wherein the step of dispensing the at least one radiation source from the seed cartridge into the lumen of the brachytherapy needle, then from the brachytherapy needle to the location in the insertion path comprises:
   moving the hollow stylet within the lumen of the brachytherapy needle to push the at least one radiation source through the lumen of the brachytherapy needle to the location in the insertion path;
   wherein the step of dispensing the medication comprises:
   dispensing the medication from the hollow stylet and into the lumen of the brachytherapy needle.

9. A brachytherapy applicator system, comprising:
   a brachytherapy needle having a lumen, a needle chuck coupled to a proximal end of the brachytherapy needle, a radiation source cartridge coupled to said coupled chuck and needle, and a stylet adapted to push a seed through the lumen, said radiation source cartridge being adapted to dispense seeds into the coupled chuck and needle, one seed at a time, said stylet being adapted to push the seed through the lumen and then retract proximal of the cartridge; and
   a medication dispensing structure comprising a reservoir constructed to store liquid medication in fluid communication with the lumen of the brachytherapy needle, the system being constructed and arranged to separately dispense both said liquid medication and seeds to substantially the same location in a patient, through the lumen of the brachytherapy needle, without removing the brachytherapy needle from the patient.

10. The brachytherapy system of claim 9, wherein the reservoir contains medication comprising anti-inflammatory material.

11. The brachytherapy system of claim 9, wherein the reservoir contains medication comprising anesthetic.

12. The brachytherapy system of claim 9, wherein the stylet comprises a hollow shaft and is sized to fit within the lumen so that sources can be dispensed by moving the stylet relative to the lumen, wherein the reservoir is joined to the stylet and is in fluid communication with the hollowed portion of the stylet to dispense medication through the stylet.

13. The brachytherapy system of claim 9, wherein the needle has a three-way fitting attached to the needle chuck and the reservoir is in fluid communication with the lumen through the three-way fitting.

14. The brachytherapy system of claim 9, wherein the needle is coated with medication.

15. The brachytherapy system of claim 9, wherein the needle comprises a dual lumen and one lumen is sized and positioned to receive radioactive sources from the cartridge and the second lumen is in fluid communication with the reservoir storing medication.

16. The brachytherapy system of claim 9, wherein a second cartridge for holding and dispensing medication is attached to the needle chuck.

17. The brachytherapy system of claim 9, wherein said radiation source cartridge further comprises a medicine reservoir for holding and dispensing medication and at least one radiation source into the needle chuck.

18. The method of claim 1, wherein the medication is dispensed at least one of before, concurrently with, and after said at least one radiation source.

19. A method of performing a brachytherapy procedure with an applicator system comprising a needle and a seed cartridge attached to the needle, the method comprising:
   inserting a brachytherapy needle having a lumen into a desired location in a patient along an insertion path extending from a proximal initial insertion point to a distal needle endpoint;
   dispensing at least one radiation source from the cartridge into the brachytherapy needle, then from the needle to a location in the insertion path; and
   flowing liquid medication through said lumen, separate from the at least one radiation source, to a location in the insertion path before the brachytherapy needle is removed from the insertion path.

20. A brachytherapy applicator system, comprising:
   a brachytherapy needle having a lumen, a needle chuck coupled to a proximal end of the needle, a radiation source cartridge coupled to said coupled chuck and needle, and a stylet configured to push a seed through the lumen, said radiation source cartridge being constructed and arranged to dispense seeds into said coupled chuck 
and needle, one seed at a time, said stylet being adapted to push the seed through the lumen and then retract proximal of the cartridge; and a medication dispensing structure comprising a reservoir constructed to store liquid medication in fluid communication with the lumen, the system being constructed and arranged to direct said liquid medication to coat a seed as said seed is pushed through the lumen by the stylet.

21. A brachytherapy applicator system, comprising:

a brachytherapy needle having a lumen, a needle chuck coupled to a proximal end of the needle, a radiation source cartridge coupled to said coupled chuck and needle, and a stylet configured to push a seed through the lumen, said radiation source cartridge being constructed and arranged to dispense seeds into said coupled chuck and needle, one at a time, said stylet being adapted to push the seed through the lumen and then retract proximal of the cartridge; and a medication dispensing structure comprising a reservoir constructed to store medication in communication with the lumen, the system being constructed and arranged to dispense said liquid medication, separate from said seeds, to substantially the same location in a patient, through the lumen, without removing the needle from the patient.

22. The brachytherapy system of claim 21, wherein the system is configured to dispense said medication into the patient.

* * * * *